United States Patent [19]

Peyman

[11] Patent Number: 5,547,473
[45] Date of Patent: Aug. 20, 1996

[54] PNEUMATIC VITRECTOMY FOR RETINAL ATTACHMENT

[75] Inventor: Gholam A. Peyman, New Orleans, La.

[73] Assignee: Syntec, Inc., Winfield, Mo.

[21] Appl. No.: 241,749

[22] Filed: May 12, 1994

[51] Int. Cl.$^6$ .................................................. A61M 1/00
[52] U.S. Cl. ........................... 604/27; 604/22; 604/26; 604/51; 604/35; 606/167; 606/170; 606/171
[58] Field of Search ............................ 604/22, 23, 26, 604/51, 118, 264, 902, 119, 30, 290, 35, 49, 27, 33, 249; 606/4, 5, 107, 166, 167, 170, 171, 172; 128/898

[56] References Cited

U.S. PATENT DOCUMENTS

| | | | |
|---|---|---|---|
| 3,776,238 | 12/1973 | Peyman et al. | 606/171 |
| 3,815,604 | 6/1974 | O'Malley et al. | 606/171 |
| 3,884,238 | 5/1975 | O'Malley et al. | 606/171 |
| 4,011,869 | 3/1977 | Seiler, Jr. | 606/171 |
| 4,246,902 | 1/1981 | Martinez | 604/22 |
| 4,530,356 | 7/1985 | Helfgott et al. | 606/171 |
| 4,577,629 | 3/1986 | Martinez | 604/22 |
| 5,037,384 | 8/1991 | Chang | 604/28 |
| 5,328,481 | 7/1994 | Wang | 604/51 |
| 5,336,175 | 8/1994 | Mames | 128/898 |

OTHER PUBLICATIONS

Tornabe, P. et al.—Pneumatic Retinopexy; Ophthalmology, Jun. 1989, vol. 95—No. 6.
Hilton, G. et al.—Pneumatic Retinopexy Ophthalmology; Apr. 1987, vol. 94, No. 4.
Hilton, G. et al.—Pneumatic Retinopexy Ophthalmology—May 1986, vol. 93, No. 5.
Retinal tears and Detachment—Krames Communications, 1100 Grundy Lane, San Bruno, CA. 94066—1994.
Peyman, G. & Schumlan, J., Intravitreal Surgery; Principles & Practice, Published 1994, Chapter 5, Appleton & Lange.

*Primary Examiner*—C. Fred Rosenbaum
*Assistant Examiner*—N. Kent Gring
*Attorney, Agent, or Firm*—Polster, Lieder, Woodruff & Lucchesi, LC

[57] ABSTRACT

A surgical instrument for the treatment of simple inferior or superior retinal detachments and a method of using the same. The surgical instrument has an elongated probe with an outer tube and an inner tube slideably engaged in the outer tube. Generally the instrument has a cutting edge and an aspiration port connected to a vacuum. A non-expanding gas delivery channel, having an outer diameter approximately that of a 36 gauge needle (0.13 mm) is adjacent the outer tube. The overall outer diameter of the probe is less than that of a 23 gauge needle (0.63 mm). In use the probe is inserted in the vitreous cavity through a small sclerotomy incision. The inner tube oscillates within the outer tube and vitreal material is drawn into the suction port, excised by the cutting edge, and removed by vacuum. Simultaneously, non-expanding gas is introduced through the gas channel to equalize intraocular pressure. The non-expanding gas migrates to the retinal tear and urges the retinal tissue toward the choroid forcing subretinal fluid from behind the retina through the tear. The instrument is withdrawn and the sclerotomy is self-sealing or requires one suture. The retinal tear is permanently attached by application of cryocoagulation or laser photocoagulation.

6 Claims, 2 Drawing Sheets

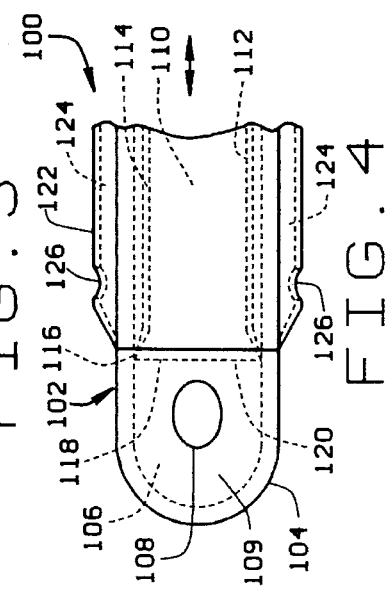
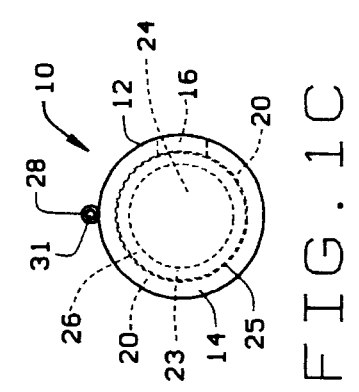
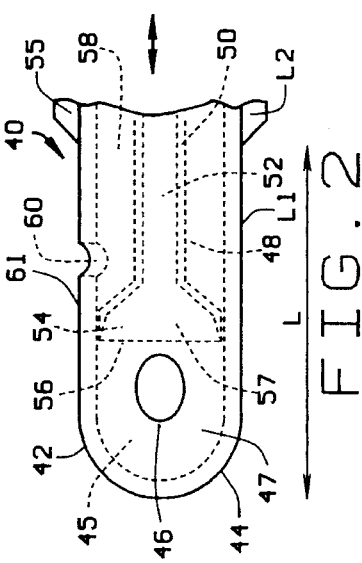
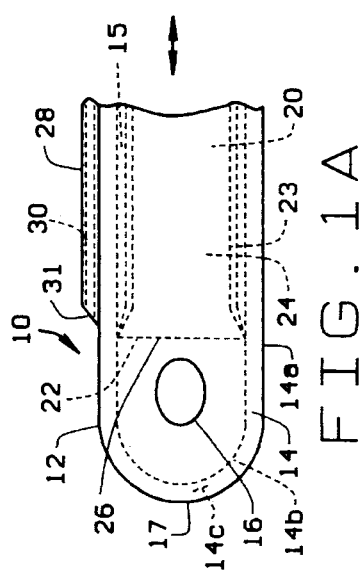
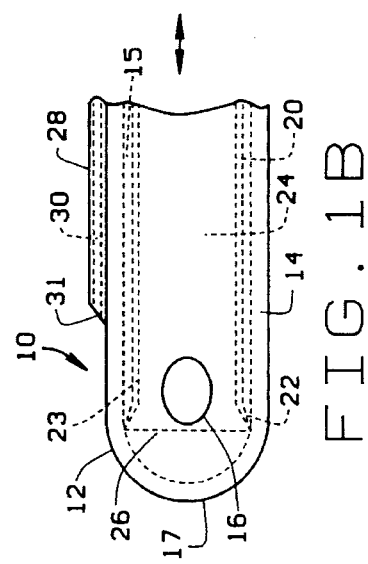
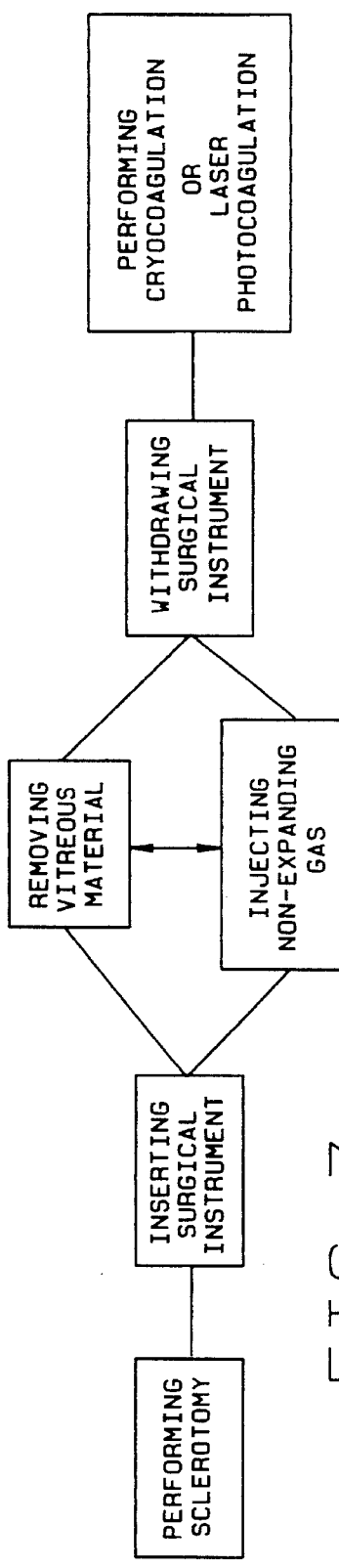

5,547,473

PNEUMATIC VITRECTOMY FOR RETINAL ATTACHMENT

BACKGROUND OF THE INVENTION

This invention relates generally to surgical instruments and, more specifically, to an ophthalmologic surgical instrument used to correct simple retinal detachments and to a method of operation for using these instruments.

Ophthalmologists use various surgical techniques to attach a detached retina. These methods have evolved over many decades. For many years scleral buckling was the method of choice. Scleral buckling requires the controlled constriction of the sclera of the eyeball until the detached retina contacts the choroid, and the creation of a chorial-retinal scar to close the retinal tear and reattach the retina. A silicone band, for example, may be wrapped around the eye. When the band is threaded under the eye muscles and tightened, the sclera of the eye buckles slightly. This buckling brings the choroid and retina together. The retina is then sealed to the choroid using laser or cryotherapy method for creating the choroid-retinal scar. Compression of the eye has obvious drawbacks including increased intraocular pressure, discomfort, trauma to the eyeball, and visual disturbances. Because it is difficult to control the compression of the eye, the technique exhibits variable results.

A relatively recent procedure includes the use of a vitrectomy system in retina surgery. A vitrectomy probe is designed to cut and remove vitreous and other material such as blood, lens remnants, and iris tissue. Generally, vitrectomy probes contain a hollow tube rotated or oscillated against an outer tube. The inner tube is driven by a small motor or by pneumatic pressure. The outer tube has an aspiration port. A cutting edge is located near the distal end of the inner tube. Tissue is drawn into the aspiration port where it is severed by the cutting edge of the oscillating inner tube and sucked into the port by vacuum, and collected in a reservoir. Many of these devices have an irrigating port through which solution is introduced inside the eye. When treating a detached retina with vitrectomy, solution is introduced inside the eye while the vitreous traction to the retina is simultaneously removed. Removal of the vitreous traction relieves its adhesion to the retina thereby allowing the retina to move toward the choroid and adhere. Furthermore, in complicated cases, the solution is introduced into the eye to lavage the retina and help remove tissue. A second instrument, such as a cryocoagulation instrument, is inserted behind the eye to attach the retina.

The vitrectomy procedure has notable drawbacks. For example, The vitrectomy probe that delivers solution is, by necessity, large. The probe must be large enough to accommodate a fluid flow tube or cannula having a bore of sufficient dimensions to allow the free flow or passage of an appropriate irrigating solution such as saline solution. Because of probe size, a relatively large incision must be made to accept the probe. Invasive procedures with large bore probes are not without risk of injury to intraocular structures. Furthermore, the incision must be sutured after procedure completion and the sutures later removed. There are other associated risks with the procedure such as increased risk of infection, increased pain, patient discomfort, visual disturbances and a relatively high degree of surgical failure.

Smaller vitrectomy probes, having only the aspirating and cutting portions and no solution administration cannula, have been used. The surgeon must, however, introduce the vitrectomy probe into one incision and introduce a second irrigating cannula through another incision to provide the flow of saline or other appropriate solution. Adding a second instrument exacerbates problems associated with the surgery.

As stated above, efforts have been made to decrease the size of the probe. Separation of the fluid infusion channel from the aspiration and cutting probe allows for the overall reduction of size of each instrument. By using a separate infusion cannula, the overall size of the aspirating and cutting probe can be reduced to approximately that of a 20 gauge needle (0.90 mm). Aspirating and cutting probes, with no infusion cannula, the size of a 23 gauge needle (0.63 mm) have been reported. Theoretically, an instrument the diameter of a 25 gauge needle (0.51 mm) could be used. This type of instrument, however, could function only for aspiration and cutting and could not provide means for the infusion of a saline solution inside the eye.

Recently detached retinas have been treated with a procedure known as pneumatic retinopexy. This procedure involves intravitreal injection of an expanding gas, such as perfluoropropane ($C_3F_8$) or sulfer hexafluoride ($SF_6$), in conjunction with the sealing of the retinal break by laser photocoagulation or cryocoagulation. In the procedure, approximately 0.3 ml to 0.6 ml of the expanding gas is briskly injected into the eye and the patient is positioned so that the expanding gas bubble exerts a force against the retina. The surgeon utilizes a second instrument to form the scar tissue to adhere the retina to the choroid.

Although pneumatic retinopexy is an improvement over older procedures, retinopexy has significant short comings. One significant drawback is that the procedure is not effective in the presence of vitreal traction. The probe or needles used to introduce the expanding gas does not have cutting and aspirating elements. Therefore, the introduction of an expanding gas in the presence of vitreal traction can exacerbate the problem by exerting pressure on the vitreous and causing the vitreous to pull against the retina, perhaps causing other tears.

Retinopexy requires extensive pre-operative preparation. Prior to the procedure, the surgeon must lower the intraocular pressure. One method of lowering the intraocular pressure is the massage technique in which the globe is pressed firmly against the orbital wall with a cryoprobe positioned near the equator.

Furthermore, injection of the expanding gas causes a rapid increase in intraocular pressure which can result in closure of the central retinal artery. Careful monitoring of the intraocular pressure during the first few hours after injection is important since this is when the bubble of expanding gas expands rapidly. Since the gas is, by its nature, expandable, the size of the resulting bubble can be difficult to control. Moreover, the use of expanding gas makes the procedure riskier in patients suffering from glaucoma. The surgeon must relieve this occlusion of the retinal artery by draining fluid from the anterior chamber of the eye or by administering drugs such as acetazolamide (Diamox) to lower intraocular pressure by reducing the production of aqueous humor. Because of the increase in intraocular pressure, the patient must be observed for at least 1 to 2 hours after surgery, increasing post-surgical recovery time and the associated costs.

Pneumatic retinopexy is limited to treating retinal detachments or breaks in the superior 8 clock hours of the retina. This is because the patient must be appropriately positioned to allow the bubble of expanding gas to press against the retinal tear. Patients having retinal tears separated by more than 60° or located in the inferior part of the retina are not good candidates for this procedure. Practically speaking, a patient having a tear in the inferior part of the retina would have to be positioned upside down to allow the bubble to contact a tear. Researchers estimate that pneumatic retinopexy can be used in only about 40% of detached retina cases. Moreover, pneumatic retinopexy is a passive procedure in that the expanding gas is injected, the patient is appropriately positioned so that the bubble migrates to the tear, and the surgeon waits for the adherance of the retina to the choria. If there is a significant amount of fluid behind the retina, the patient must be appropriately positioned and the surgeon must wait, sometimes 24 to 48 hours, for the bubble to force the fluid from behind the retina before the surgeon can preform cryocoagulation or laser photocoagulation to attach the retina. There is also a related problem, known to practioners the "fish egg" phenomenon where multiple small bubbles are introduced into the vitreal during expanding gas injection, and one or more small bubbles pass through the retinal tear and accumulate behind the retina. If multiple bubbles appear, the eye must be thumped to cause the coalescence of the bubbles. If that fails, the patient must be positioned so that the small bubbles migrate to a point opposite the tear and accumulate into one larger bubble. This can require an additional 24 hour waiting period. The delay can cause increased discomfort and inconvenience for the patient, increased costs associated with the procedure, and increased risks such as congestion of central retinal artery.

Although prior art surgical instruments and techniques represented significant advances in their time, they all suffer drawbacks. The older instruments, especially those that infuse solution simultaneously with aspirating and cutting, are relatively large. Since the use of such a probe is an invasive technique there is increased risk of infection and trauma to intraocular structures. Post-surgical suturing of the wound is required. Such complications and risks are generally unnecessary and unreasonable when performing a procedure to correct a simple retinal detachment. Furthermore pneumatic retinopexy does not allow for removal of vitreous material, is appropriate only in superior tears or detachments, can cause a rise in intraocular pressure, and can be difficult to control.

I have found that improvements in instruments and technique disclosed hereinafter enable simple retinal detachment to be treated on an outpatient basis without the effects common with known prior art instruments and procedures.

SUMMARY OF THE INVENTION

It is a principle object of the present invention to provide a surgical instrument for the treatment of simple detachment of the retina having a probe portion that combines a cutter, aspirator, and small bore gas delivery tube with the approximate overall diameter of a 23 gauge needle (0.635 mm) or less.

Yet another object of the present invention is to provide such an instrument in which the gas delivery tube accommodates the passage of a non-expanding gas only and does not normally accommodate the passage of a fluid.

Still another object of the present invention is to provide such an instrument in which the gas delivery tube of the instrument has a diameter in the range of approximately a 36 gauge needle (0.13 mm) to a 30 gauge needle (0.30 mm).

Another object of the invention is provide such a surgical instrument that allows for the cutting and removal of vitreous material while infusing a non-expanding gas, such as air, to maintain intraocular pressure.

Yet another object of the present invention is to provide such a surgical instrument that uses non-expanding gas to force fluid from behind the detached retina and to urge the detached retina against the choroid for attachment.

Another object of the present invention is to provide a method of correcting simple detached retina, either superior or inferior, with such a surgical instrument.

Another object of this invention is to provide a surgical procedure and instrument for that procedure in which a detached retina can be corrected routinely in less than one-half hour.

Another object of the invention is to provide a surgical procedure and instrument for that procedure which reduces patient observation time upon completion of this procedure.

Yet another object of the invention is to provide a surgical instrument and procedure which reduces risk of congestion of the central retinal artery.

Still another object of this invention is to provide a surgical instrument and procedure which reduces the need to suture the incision made in the eye.

These and other objects will be apparent to those skilled in the art in view of the following description and accompanying drawings.

In accordance with the invention, generally stated, a surgical instrument for repairing simple retinal detachment, and method of using the instrument, are provided wherein the entire probe portion of the instrument has a diameter of a 23 gauge needle (0.635 mm) or less. In the preferred embodiment, the probe includes two concentric tubes. The outer tube has an aspirating port in it. The inner tube has a cutting edge at the distal end. The inner tube is driven in an oscillating or rotating fashion. The outer and inner tubes cooperate to excise and remove semi-solid material from the eye. A side channel, having the diameter in the range of a 30 gauge to a 36 gauge needle, is adjacent the outer tube and serves as a cannula for the injection of air or non-expanding gas inside the eye. The diameter of the gas channel is so small that normally only gas can pass through it. As will be appreciated by those skilled in the art, at high enough pressure, fluid can be forced through even a small channel. I have found that the small probe described herein greatly reduces recovery time and simplifies heretofore complicated procedures.

In the method form of the invention, the instrument is inserted through a small surgical incision into the vitreous cavity of the eye. The non-expanding gas is injected through the non-expanding gas channel and, simultaneously, liquid, vitreous and fibers are aspirated and cut by the cutting element and removed by vacuum through the inner tube. The injection of the non-expanding gas, simultaneously with the removal of liquid vitreous creates a balance within the eye, maintaining intraocular pressure at near normal levels. After injection of a sufficient quantity of non-expanding gas, the instrument is withdrawn by continuous aspiration and cutting until the instrument exits from the incision site. The gas is injected with the patient in an inclined or prone positioned and rises towards the optic nerve, thereby forcing the subretinal fluid through the peripheral retinal tear and simultaneously positioning the retina against the choroid. The retina, which is now positioned to be attached, can be coagulated through the conjunctiva by cryocoagulation or through the pupil using a laser or other similar means. Because of the small size of the instrument the surgical wound may be self-sealing or, at the most, require a single small suture. Since the injection of non-expanding gas inside the vitreous cavity is easily controlled and balanced with the removal of vitreous material, a serious increase in intraocular pressure is avoided. The method includes making a small sclerotomy incision; inserting the surgical instrument into the vitreal cavity through the sclerotomy incision; removing vitreous material from the vitreous cavity while injecting, simultaneously, a non-expanding gas into the vitreal cavity to maintain intraocular pressure at a near normal level; the non-expanding gas exerting pressure against the retina, moving it toward the choroid; withdrawing the instrument from the sclerotomy incision; and attaching the retina to the choroid of the eye. The procedures can be used to (i) correct approximately 85% of detachments, including tears in the inferior portion as well as superior part of the retina, and (ii) correct multiple tears.

BRIEF DESCRIPTION OF THE DRAWINGS

FIG. 1A is a view in side elevation, partly broken away, of one illustrative embodiment of probe for the surgical instrument of the present invention, the inner tube being illustrated in a first or retracted position;

FIG. 1B is a view corresponding to FIG. 1A, the inner tube being illustrated in a second or extended position;

FIG. 1C is an end view thereof;

FIG. 2 is a view in side elevation, partly broken away, of a second illustrative embodiment of probe for the surgical instrument of the present invention;

FIG. 3 is a view in side elevation, partly broken away of a third illustrative embodiment of probe for the surgical instrument of the present invention;

FIG. 4 is a view in side elevation, partly broken away of a fourth illustrative embodiment of probe for the surgical instrument of the present invention;

DESCRIPTION OF THE PREFERRED EMBODIMENT

Figure 6:
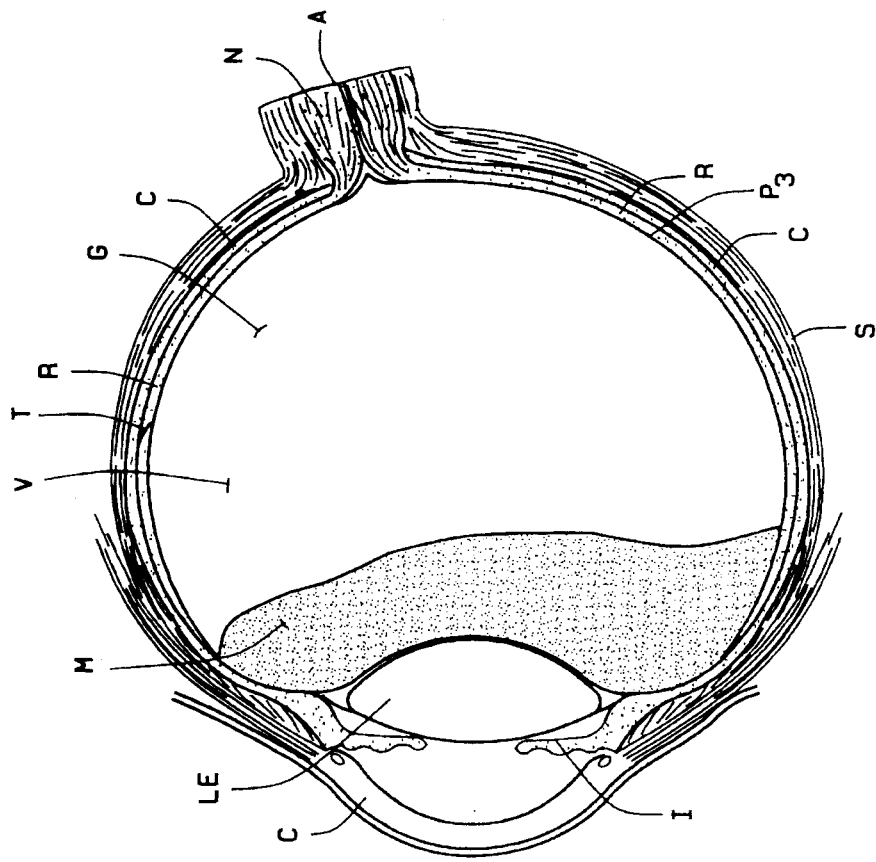
FIG. 6 is a cross section view of an eyeball, illustrating the eye after such surgery; and, FIG. 7 is a block diagramatic view illustrating the surgical method employing the surgical instrument of the present invention.

Referring now to the drawings, one illustrative embodiment of surgical instrument of the present invention is indicated generally by reference numeral 10 in FIGS. 1A–1C. Instrument 10 is a pneumatic vitrectomy probe constructed so as to have a generally elongated probe portion 12 and a handle section (not shown). Probe 12 includes an outer or first tube 14 and an inner or second tube 20.

Tube 14 has an outer surface 14A, and interior surface 14B separated by a material thickness 14C therebetween, and a closed distal tip 17. The surfaces 14A and 14B define an inner bore 15. Tube 14 is formed from surgical steel or other appropriate material. Tube 14 is sealed except for a aspiration port 16 formed through the material thickness 14C through the surfaces 14A and 14B.

The inner tube 20 is sized so as to be generally concentric with and to be slideably engaged within bore 15 of outer tube 14. Inner tube 20 is slightly under-sized relative to bore 15 so that tube 14 can move or oscillate back and forth inside bore 15. As will be appreciated by those skilled in the art, instrument 10 also can be designed so that the tube 20 rotates about a central axis of and within bore 15. The tube 20 has a slightly flared distal end 22 and an elongated hollow tubular body section 23. The hollow body section defines a suction path 24. Distal end 22 of tube 20 defines an annular orifice 25. An edge 26 surrounding orifice 24 is constructed to act as a razor sharp cutting edge. Orifice 25 and suction path 24 are operatively connected to a conventional suction apparatus (not shown) which is controlled by the surgeon to exert appropriate suction through the instrument during use, as will be described below.

The tube 20 is driven by an appropriate conventional power source, such as an electric motor or pneumatic power so that it oscillates, back-and-forth, within chamber 15 as previously described. FIG. 1A illustrate tube 20 in a retracted position and FIG. 1B illustrate tube 20 in an extended position. The suction apparatus and power source can be contained in a conventional console and appropriately connected to instrument 10. Tube 20 oscillates while a suction is applied through path 24 and orifice 25. Semi-solid material, such as intraocular vitreous, is pulled into aspirating port 16 and excised as cutting edge 26 moves past port 16 in a guillotine fashion. The severed material is sucked, through orifice 25 and path 24 into the suction apparatus for disposal.

A gas delivery channel 28 is adjacent outer tube 14. In this embodiment, channel 28 is an elongated tube extending along the length of outer tube 14. Channel 28 is positioned 90° to port 16. Channel 28 has an internal bore 30 terminating in an opening 31. Channel 28 is connected to a conventional source of non-expanding gas, such as air, which also can be provided through the aforementioned console. As will be appreciated by those skilled in the art the term "non-expanding" gas means a gas which keeps eye pressure nearly normal, without requiring monitoring, during the procedure described below. Channel 28 is quite small in diameter, having the diameter of between approximately that of a 36 gauge needle (0.10 mm) and that of a 30 gauge needle (0.30 mm). Channel 28 allows the passage of non-expanding gas, such as air, through bore 30 but normally cannot accommodate the passage of a liquid, such as saline solution. It should be noted that the use of small gauge channel 28 to deliver only non-expanding gas allows the overall outer diameter of probe 12 to be quite small, being less than that of a 23 gauge needle (0.64 mm), and preferably less than that of a 25 gauge needle (0.51 mm).

FIG. 2 illustrates another embodiment of a surgical instrument of the present invention indicated generally by reference numeral 40. Instrument 40 includes a generally elongated probe 42. Probe 42 is defined by a sealed first or outer tube 44 having an internal bore 45 formed in it. An aspirating port 46 is formed in a side 47 of tube 44. A second or inner tube 48 is slideably positioned within bore 45. Tube 44 and tube 48 are formed from surgical steel or other appropriate material. Tube 48 has an elongated, tubular body section 50 having an aspiration or vacuum channel 52 formed in it. Body section 50 terminates at its distal end in a flared end 54. In the embodiment illustrated, end 54 is a frusto-conical element formed to provide a razor sharp cutting edge 56. The edge 56 surrounds and defines an annular orifice 57. Body section 50 is slightly under-sized relative to bore 45 creating a gas flow channel 58 around body section 50.

A gas port 60 is formed in a side 61 of tube 44, positioned approximately 90° relative to port 46, gas port 60 operatively communicates with gas flow channel 58. The channel 58 normally is large enough to allow only the passage of non-expanding gas, such as air. Preferably the channel 58 has a cross-sectional area between approximately the size of a 36 gauge needle (0.10 mm) and the size of a 30 gauge needle (0.30 mm). Because of the extremely small size of channel 58, which allows only the passage of non-expanding gas, the overall outer diameter of probe 40 is quite small and preferably is approximately the diameter of a 23 gauge needle (0.64 mm) or less. Tube 48 is connected to a conventional drive console, as previously described, (i) to provide power, either electric or pneumatic, to drive tube 48 within tube 44; (ii) to provide appropriate controlled suction through vacuum channel 52 and orifice 57; and (iii) to provide a source of non-expanding gas to channel 58.

FIG. 3 illustrates another embodiment of a surgical instrument of the present invention, indicated generally by reference numeral 70. Instrument 70 is defined in part by an elongated probe section 72. Probe 72 includes a first or outer tube 74 having an internal longitudinal bore 76 formed in it. Tube 74, again, is constructed from surgical stainless steel, for example. A bevel 78 is formed at the distal end of tube 74, such that the tube end defines an annular razor sharp, cutting edge 80. A concentric second or inner tube 82 is slideably engaged in bore 76. The tube 82 extends distally beyond bevel 78. Tube 82 has a distal end 84. A vacuum channel 86 is formed in and extends through tube 82. Channel 86 terminates in a suction orifice 88, formed through a side of tube 82. Vacuum channel 86 is operatively connected to a conventional vacuum source (not shown) controllable by the surgeon. Tube 82 is connected to a conventional power console (not shown) to provide oscillating power to tube 82. Tube 82 oscillates back-and-forth within tube 74. In use, vitreous or other semi-solid intraocular tissue is drawn into port 88 by a controlled suction and severed by cutting edge 80 upon the oscillation of tube 82. A non-expanding gas delivery tube 90, with internal bore 92 and orifice 93, is provided adjacent external tube 74. Tube 90 is very small, normally allowing only the passage of non-expanding gas through bore 92. Tube 90 has an outer diameter approximately between the diameter of a 36 gauge needle (0.10 mm) and the diameter of a 30 gauge needle (0.30 mm). Therefore, the overall diameter of probe 72 can be and is quite small, approximately that of a 23 gauge needle (0.64 mm) or less.

FIG. 4 illustrates yet another embodiment of the instrument of the present invention, indicated by reference numeral 100. Instrument 100 includes an elongated probe section 102 operatively associated with a conventional handle (not shown). Probe 102 includes a first elongated tube 104 defining a longitudinal bore 106. Tube 108 has an aspirating port 108 formed in a side 109 of it. A second or inner tube 110 is slideably engaged in bore 106. Tube 110 has a hollow, elongated body section 112 defining a vacuum channel 114. The body section 112 terminates at a flared section 116. Flared section 116 is formed to provide by a razor sharp cutting edge 120 surrounding an annular orifice 118.

A third tube 122 surrounds, but is slightly spaced from, tube 104, to create an non-expanding gas channel 124 between the respective tubes 104, 122. Preferrably a plurality of gas ports, such as 126, are formed in tube 122 as to communicate with channel 124. Channel 124 is very small, normally allowing only the passage of non-expanding gas through ports 126. Therefore, the overall outer diameter of instrument 100 can be and is very small, approximately that of a 23 gauge needle or less.

Figure 5:
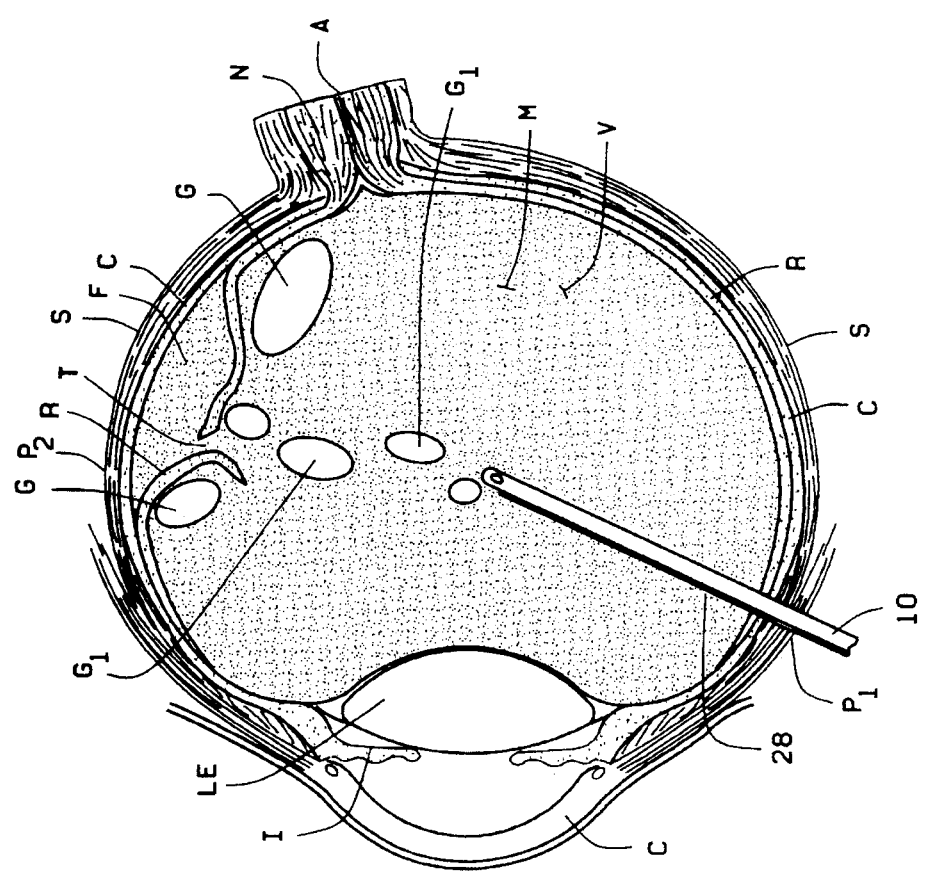
FIG. 5 is a cross section view of an eyeball illustrating an embodiment of the probe for the surgical instrument of the present invention inserted therein, demonstrating a method for performing surgery with the instrument.

FIGS. 5–7 illustrate the use of an embodiment of surgical instrument of the present invention to perform a simple retinal reattachment. Instrument 10 is inserted inside eyeball E. As will be appreciated, the depth of insertion required for applicational use may vary. I have found that the instrument 10 need only to be inserted to a depth of 4 mm for certain procedures. The anatomical structures of the eyeball include sclera S, choroid C, iris I, lens LE, optic nerve N, vitreous cavity V, vitreous material M, central retinal artery A and retina R. FIG. 5 illustrates a tear T in retina R and the retina R is pulled away from choroid C. There also is sub-retinal fluid F behind retina R. The surgeon makes a small incision in the sclera S to form a sclerotomy of less than 1.0 mm. The sclerotomy is made at either the pars plana $P_1$ or pars plicata $P_2$, 2 to 5 mm behind the limbus. The surgical knife is withdrawn and the patient is positioned either in the supine, sitting, or prone position. The surgical instrument of the present invention, shown generally as reference numeral 10, is inserted through the sclerotomy. The tip of instrument 10 is observed by the surgeon in the vitreous cavity V through an operating microscope (not shown), an indirect ophthalmoscope (not shown), or a slit lamp (not shown), for example. Non-expanding gas G is injected through gas channel 28 while, simultaneously, vitreous material M is aspirated, cut and suctioned away by the cutting and aspirating action of the concentric tubes of instrument 10, as previously described. Infusion of non-expanding gas G, with the simultaneous removal of vitreous material M, creates a balance, maintaining intraocular pressure at a near normal level. Gas G migrates toward retina R and tear T exerting pressure against retina R, moving it toward choroid C. Subretinal fluid F is forced out through tear T allowing the movement of retina R toward choroid C, simultaneously positioning retina R against the choroid for attachment. After the injection of a sufficient amount of non-expanding gas, instrument 10 is gradually withdrawn until it exits from the sclerotomy site. Continuous aspiration and cutting may be employed during removal of the instrument. Retina R, which is now positioned for attachment, can be coagulated using cryocoagulation or laser photocoagulation through the pupil. Due to the very small size of instrument 10, the sclerotomy is small and may be self-sealing or, at most, may require a single suture to close.

Because the injection of non-expanding gas inside the eye is balanced with the removal of vitreous material M, a serious increase in intraocular pressure is not produced. This minimizes the chance of closure of the central retinal artery A and also reduces the time of post-surgical observation. Since an appropriate volume of non-expanding gas G can be infused without increasing intraocular pressure, sufficient non-expanding gas G can be introduced to repair tears in the inferior portion $P_3$ of the retina, as shown in FIG. 5. Also, any existing vitreal traction can be removed to permit retina R to be positioned against the choroid C. Non-expanding gas G is eventually absorbed as the eyeball refills with naturally produced aqueous humor.

It will be apparent to those skilled in the art that various modifications may be made in the instrument and the method of using the same without departing from the scope of the appended claims. Therefore, the foregoing description and accompanying drawings should be viewed as illustrative only and not in a limiting sense. Merely by way of example the probe employed with the instrument described may have first and second diameter L portions. Thus, as shown in FIG. 2, the overall length of the probe 42 is divided into a first diameter part L1 and a second diameter part L2 by a shoulder 59, the diameter part L2 being substantially larger than the diameter part L1. Although ophthalmological probes up to 40 mm in length are known, a probe having a length of 12 mm to 14 mm would be sufficient for most retinal procedures. The part L1 in operational use need only have a length of about 4 mm to about 14 mm to function well in the procedures described above. Any additional probe length and handling part for the instrument may correspond to the larger diameter part L2, or similar equivalent structure. While the increased diameter part L2 is illustratively shown in conjunction with and respect to the probe 42 of instrument 40, those skilled in the art will recognize that similar variable diameter configurations may be used with all of the embodiments described.

I claim:

1. A method for the reattachment of a detached retina comprising the steps of:

making a small sclerotomy incision in the eyeball;

inserting a surgical instrument into the vitreous cavity of the eye through said sclerotomy incision, said surgical instrument having means for cutting and removal of vitreous material, means for aspirating vitreous material, and means for injection of a non-expanding gas into the vitreous cavity;

removing vitreous material from said vitreous cavity;

injecting, simultaneously, non-expanding gas into said vitreous cavity to maintain the intraocular pressure within said cavity at a near normal level to urge the retina toward the choroid;

withdrawing said instrument from said sclerotomy incision; and attaching said retina.

2. The method of claim 1 wherein said step of attaching said retina further comprises the step of performing cryocoagulation to attach said retina.

3. The method of claim 1 wherein said step of attaching said retina includes applying laser energy to perform laser photocoagulation of said retina.

4. The method of claim 1 wherein said means for delivering non-expanding gas into said vitreous cavity further comprises injecting a non-expanding gas through a gas delivery channel, said gas delivery channel having an outer diameter approximately that of a 36 gauge needle (approximately 0.10 mm) to approximately that of a 30 gauge needle (approximately 0.30 mm).

5. The method of claim 1 wherein said surgical instrument has an outer diameter of approximately that of a 23 gauge needle (approximately 0.63 mm) or less.

6. A method for reattaching a detached retina comprising:

making a small sclerotomy incision in the eyeball;

inserting a surgical vitrectomy instrument into the vitreous cavity of the eyeball through said sclerotomy incision;

cutting and removing vitreous material from said vitreous cavity with said vitrectomy instrument;

injecting simultaneously with removal of vitreous material a non-expanding gas into said vitreous cavity through a small bore gas delivery channel to maintain the intraocular pressure within said cavity at near normal level, said gas exerting pressure against the retina, moving it toward the choroid of the eye;

withdrawing said vitrectomy instrument and said small bore gas delivery channel from said sclerotomy incision; and attaching said retina to the choroid of the eye.

\* \* \* \* \*